United States Patent [19]

Sulc

[11] Patent Number: 5,120,222

[45] Date of Patent: Jun. 9, 1992

[54] DENTAL ATTACHMENT STRUCTURE

[76] Inventor: Josef M. Sulc, 145 Mountain Rd., Wilton, Conn. 06897

[21] Appl. No.: 578,396

[22] Filed: Sep. 7, 1990

[51] Int. Cl.⁵ .......................................... A61C 13/225
[52] U.S. Cl. ..................................... 433/181; 433/182
[58] Field of Search ............... 433/181, 182, 180, 183, 433/167

[56] References Cited

U.S. PATENT DOCUMENTS

| | | | |
|---|---|---|---|
| 1,199,109 | 9/1916 | Philbrook | 433/182 |
| 4,540,367 | 9/1985 | Sulc | 433/182 |
| 4,820,158 | 4/1989 | Speckmann | 433/181 |
| 4,957,438 | 9/1990 | Bax | 433/181 |

Primary Examiner—Cary E. O'Connor
Attorney, Agent, or Firm—Pennie & Edmonds

[57] ABSTRACT

The present invention is a dental structure for removably mounting a dental appliance, including a partial denture, bridge, or similar dental appliance in an oral cavity. The dental structure includes an improved male member comprising a substantially cup-shaped body, including a base, a cylindrical wall extending form the base, a projection extending from the base in the same direction as the wall, and a relatively large rectangular stop member that provides a positive contact with an upright wall of a female member. This new and improved feature provides an additional stabilizing contact surface and also serves as a stop surface to prevent the male member from pivoting toward the upright wall of the female member when the male member is fully seated on the female member.

17 Claims, 4 Drawing Sheets

DENTAL ATTACHMENT STRUCTURE

BACKGROUND OF THE INVENTION

1. Field of the Invention

The present invention relates to a dental attachment structure that removably supports, in an oral cavity, one end of an appliance or an appliance at a single point, but is not so limited and may find use in other than single point support prothesis. The appliance can be any one of a partial denture, an overdenture, and bridgework. Specifically, the present invention relates to an improvement of the male member of the dental attachment structure that prevents the free end or the unsupported end of the appliance from lifting off the edentulous ridge that supports the appliance.

2. Description of the Prior Invention

U.S. Pat. No. 4,540,367 (Sulc '367) discloses a dental attachment structure similar to the present invention and is incorporated herein for the disclosure of the male member and female member of the dental attachment structure. The description of the Sulc '367 patent, as substantially described in the patent, follows:

A dental attachment structure 10 comprises an extracoronal connector (hereafter "connector") used for mounting an appliance in the oral cavity as shown in FIG. 1. The connector includes two components, including a female member 12 and a male member 14. A support structure 16, illustrated in FIG. 3, for example, serves in one form of the invention as a receptacle for the male member in the base of the appliance. However, the male member may be received directly in the base of the appliance 26 thereby to obviate the need of a receptacle as shown in FIG. 4.

The female member 12 of the connector remains in the oral cavity permanently mounted on a natural or abutment tooth. A full crown or inlay 18 formed on the tooth supports the female member. As illustrated, the female member 12 has the general configuration of an L-shaped structure. The L-shaped structure comprises a retention plate 20 and a base 22 extending from the retention plate. The base terminates in a cup-socket 24. The retention plate is configured to provide a portion 20a and a portion 20b. With reference to FIG. 5, the portion 20b of the retention plate provides the situs of attachment of the female member to the crown of the natural tooth. As may be seen, the crown substantially surrounds the portion 20b and is received between that portion and portion 20a, within a cut out region 20c. The portion 20a resides in juxtaposition to the outer surface of the crown and supports the female member substantially along the depth of the structure. The portion 20b also acts to compensate for any torque which may develop as the male member 14 and the appliance 26 is removed from the oral cavity.

The base 22 may be of any particular shape and serves the purpose of supporting the socket 24 at a disposition closely spaced from portion 20a of retention plate 20. The socket 24 takes the form of a cup having an upstanding side wall. The outer surface of the side wall of the socket generally is slightly conical in outline and merges with the base 22. The taper is an outward taper in the direction of movement of male member 14. The inner surface of the side wall is contoured to form a necked-down region or constriction 24a in the form of a convex arc shaped profile.

The female member 12 preferably is formed of a metallic material, such as a metal which conventionally finds use in the field of dentistry. The male member 14 preferably is formed of a plastic material having sufficient strength and durability to permit the repeated connecting and disconnecting movements telescopically of the male and female components in locating the appliance in and removing the appliance from the oral cavity. The material of the male member should also provide a measure of resilience to permit a snap retention in mounting the male and female members. In addition, the material of the male member should develop a retaining friction between the male and female members to retain the appliance in a positive manner in the oral cavity, yet permit removal of the appliance from the oral cavity when desired. The male member, accordingly, may be formed of strong nylon, a material that also has been found to eliminate problems of wear of the female member. In this connection, the male member will absorb all wear and as wear increases, the male member is replaceable by a new male member. As will be described, the replacement technique whereby one male member is replaced by another is not complex and repeatable, and may be carried out with complete accuracy of alignment between the male member and female member.

The male member 14 of the connector is also characterized by substantially a cup-shaped structure. As such, the male member includes a wall 14a which extends from a base 14b. In addition, a projection 28 extends from the base, along the axis of the wall 14a. The projection has an outer contour which generally is complementary to that of the inner surface of the side wall of socket 24. To this end, the projection includes a constriction at about the midpoint of its length which merges, at its ends, in a convex arc toward the base 14b and the end of the projection. The constrictions allow for a snap fit retention and a mount which will permit a substantial universal movement capability of the appliance. The convex arcs of the projection 28 have equal radii. The concave arcs along the inner surface of the side wall of socket 24 likewise have equal radii, somewhat greater than that of the convex arcs to permit such movement. The male member also includes a pair of ridges 30, 32 formed on the outer surface of the wall 14a. Each ridge extends completely around the wall, and the ridges are spaced apart so that one ridge is near the base 14b and the other ridge is near the opening between the projection and the inner surface of the wall.

The appliance 26 which may be a partial denture, a bridge or similar dental prothesis may be formed of a dental acrylic. The appliance itself is supported by a male member or a pair of male members which telescopically cooperate with a female member or a pair of female members in mounting the appliance. This support may be a direct support, illustrated in FIG. 4, or the appliance may be supported by the combination of the receptacle 16 and the male member received in the receptacle, illustrated in FIG. 3.

FIG. 3 illustrates the receptacle 16 as having a shape like that of the male member 14. The receptacle is embedded in the dental acrylic of the appliance. Typically, the receptacle may be embedded in the appliance during the forming process which is carried out according to conventional techniques. The receptacle 16 provides an internal surface which is complementary to the external surface of wall 14a of male member 14. Thus, a pair of grooves 34, 36 are formed around the internal surface of a wall 16a, and the grooves are spaced to accommodate the ridges 30, 32, respectively. The receptacle may be formed of the same material used for the female member 12, and a serrated outer surface 38 along the wall 16a toward the appliance will maintain the embedded relationship as seen in FIG. 3.

FIG. 3 also illustrates the male member 14 in position spaced from a seated position within the receptacle, while FIGS. 6 and 7 illustrate the male member seated within the receptacle and removably secured by the interaction of ridges 30, 32 within the grooves 34, 36, respectively. Whether the male member 14 is situated within the receptacle 16 (FIG. 3) or directly embedded in the dental acrylic of the appliance (FIG. 4), the male member may be removed from the seated position for replacement, or any other purpose. The manner of removal of the male member will be discussed below.

Referring to FIG. 1, the appliance 26 which is illustrated comprises a partial denture formed by a plurality of teeth 40, 42 . . . . 48, and a pair of connectors 10 support the partial denture between a pair of abutment teeth 50, 52. Each abutment tooth may be provided with a full crown or inlay 18, as previously discussed. The appliance 26 may be received into the oral cavity and secured rather easily. To this end, the appliance is moved to position the projection 28 of the male member 14 above the opening into socket 24 of the female member 12. The appliance may be secured in the oral cavity at either a single or a multiple of locations. The end of projection 28 is generally ball-shaped in outline and it moves with a snap fit through the neck-down region 24a as the projection enters into the socket. At the same time the wall 14a of the male member 14 slides along the outer surface of the socket 24 to the fully received position. The friction between the walls and the snap fit of the ball and socket connection provide a positional and positive securement with the aforesaid movement capability, of the appliance in the oral cavity. Both the male member 14 and receptacle 16 are formed with a cutout to accommodate the base 22 within the region of support of socket 24. The cutout 14c in the wall of male member 14 and cutout 16a in the wall of receptacle 16 may be seen in FIGS. 3 and 6.

As previously discussed, the male member 14 of connector 10 not only is replaceable, it is replaceable with complete accuracy. Therefore, as problems of wear, retention, and so forth develop, the restoration may be returned to the original state without the large cost usually associated with an entire restoration.

FIGS. 8 and 9 illustrate a male member 14 to be removed from the acrylic base of the appliance 26 (not shown) and a male member to be replaced in the acrylic base of the appliance, respectively. The male member may be removed and replaced in both forms of the invention wherein the male member is received directly or in combination with a receptacle 16. The one-piece construction of the male member, and the material from which it is fabricated permit these actions, as will be set out. The return of the restoration to the original condition is carried without any destructive action to the acrylic base of the appliance requiring a build up of acrylic material to affix the new component of male member in the existing appliance. As may be apparent, if a build up is required there may be no assurance that the new component will be placed back exactly to the position from which the old component was removed. Even a small deviation will result in problems with the male member not properly engaging the female member when the appliance is seated in the oral cavity.

A cutting tool 56 is provided to remove the male member 14 from the acrylic base of appliance 26 or the receptacle 16. The cutting tool includes a handle 58 and a blade 60. The blade is annular in outline for receipt between projection 28 and a inner surface of wall 14a of the male member. The cutting tool, in essence, cores out the projection and that portion of a base 14b which supports the projection. A stop 62 in the form of a surface interacts with the end of the projection to limit movement of the cutting tool in travel toward the acrylic base only to the plane of the outer surface of base 14a. When the projection and portion of the supporting base is cored out it may be easily removed. The hollow ring which remains, then, may be collapsed inward and removed. A seating tool 64 serves in mounting a new male member 14 in the location vacated by the male member which is replaced. To this end, the seating tool includes a handle 66, a prong 68 in the form either of a plurality of fingers with a cylindrical tip or a totally cylindrical finger, or the equivalent, and a base 70 which interacts with projection 28. The base and finger (or tip) act to snap the male member into place. The male member will be physically restrained by interaction of ridges 30, 21 in grooves 34, 36, respectively.

Bonded restoration techniques for use with connectors for removable appliances eliminate the need for placing a full crown over an abutment tooth. Instead, a relatively small metal flange is fabricated. The surfaces of the abutment tooth and the metal flange that will come in contact are etched with acid solution to provide microscopic undercut areas on the tooth surface and on the metal for bonding of the metal flange to the selected surface (s) of the tooth. Thus, a missing tooth may be replaced by etching the adjacent teeth in the areas where flanges carrying the replacement tooth will be bonded. This technique now is very popular because it is more conservative than conventional crowns (much less of the natural tooth structure is removed) and less costly. The success of this type of restoration, however, depends to a great measure on the ability of the metal flange to remain securely bonded to the abutment tooth, and not to become dislodged by forces as may be developed during the chewing cycle.

The connector of the invention provides an ideal construction since the male member of nylon provides a cushioned flexible connection that will protect the bond and assist in prevention of the female member from breaking away from the abutment tooth. The overall concept in the connector of the invention, in addition to the resiliency and flexibility of the male member, includes the provision of a small space between the male and female members to allow for up and down movement of the members as well as hinge action between the members.

FIG. 10, illustrates a cross-sectional view of a portion of socket 24 of female member 12 and the male member 14. The projection in a quiescent or non-chewing condition, extends just beyond the neck 24a to provide a space between the lower surface of base 14b and the upper surface of the socket. The space allows for movement of the male member which supports the appliance in the direction of arrow 72 beyond a full snap position of receipt of the male member into the socket. A limiting factor in the vertical movement of the appliance is how much the tissue (gums) may compress. When the appliance is seated in the oral cavity, the saddle 74, for example of FIG. 3, of the appliance comes into full contact with the gums just as the projection of the male member snaps over the socket of the female member. Then, under additional load on the appliance, during chewing, the appliance can settle and recoil back as the tissue resiliency will allow. In this manner, the forces that are generated during the chewing cycle are distributed over the entire edentulous ridge area that supports the appliance. On the other hand, if the fit between the male and female members of the connector 10 was a totally rigid snap fit, the appliance could not move any further down into a heavier contact with the tissue. Consequently, all the extra force would have to be absorbed by the abutment tooth. The space, however, in a quiescent or passive position, in which the appliance is fully seated and the male member just engages below the neck in the snap fit in the female member, but having no extra load on the appliance and no compression of the tissue, will accommodate movement of the appliance when pressure is applied thereto during the chewing cycle for example. The dimension of the space will equal the maximum possible additional downward movement that the appliance may undergo. The invention provides a unique way of creating the space as well as the receptacle for placement of the male in the acrylic base material. Reference now may be directed to FIGS. 11 and 12.

FIG. 11 illustrates a male member 14' which is a replacement component and FIG. 12 illustrates a male member 14" which is a fabricating component. The difference between the two male members resides in the thickness of each base 14b' and 14b", and consequently the length of the projections 28, and 28" respectively. Male member 14' has a base having a thickness "A", while fabricating male member 14" has a base of somewhat greater thickness "B". In the appliance fabrication process, the fabricating male member is used in the following manner. The completed bridge carrying the female member is placed on a plaster working model of the mouth of the patient. The bridge rests on this model in exactly the same position as it will be in the oral cavity. The model includes a duplication of the ridge areas on which the appliance will rest. The fabricating male member is snapped into the socket of the female member. The fabricating male member rests directly on the top surface of the socket of the female member as the projection snaps fully inside the socket. The fit is a snug fit and provides no space to allow for any movement. The appliance which may be a partial denture is now formed on the model of the mouth. The acrylic base material will flow and harden around the outside of the fabricating male member and over the duplication of the jaw. Artificial teeth are set into the hardening acrylic. After the acrylic completely cures, the partial denture is removed from the model. This technique is the technique carried out in the form of the invention which does not utilize the receptacle 16. The process is continued by coring out the center portion of the fabricating male member, collapsing the remaining walls inward, any small pointed instrument may be used, disengaging the undercut ridges, and then pulling the remaining part of the fabricating male member out of the acrylic. An exact duplication of the outside shape of the fabricating male member including the grooves 34, 36 will remain in the hardened acrylic. The male member now may be seated by the seating tool and snapped into the acrylic base and socket created by the fabricating male member. A free space, however, will remain between the top surface of the socket of the female member and the inside upper surface of the male member. The space will equal the difference between the dimensions "A" and "B".

APM-Sterngold Catalog, "A Selection Guide to Attachments and Precious Alloy (1987)", pp. 6-8 and 10, discloses dental attachment devices similar to that of the Sulc '367 patent, ERA. In addition, the catalog discloses an alternate embodiment of the ERA male attachment, the OCTOLINK. The OCTOLINK male is formed with a metal projection that screws into the metal base wall of the male housing rather than being formed with one piece nylon.

The features of the present invention is an improvement of the male ERA and the male OCTOLINK. The differences and the improvement of the present invention will be apparent and better appreciated from the following description.

SUMMARY OF THE INVENTION

The present invention is an improved dental attachment device which includes male and female members which are similar to those described in the Sulc '367 patent, the disclosure of which has been incorporated herein. Specifically, the present dental attachment structure removably mounts a dental appliance or one end of the same which may be a partial denture, a bridge, or a similar dental appliance, in an oral cavity. The female member has an upright wall which mounts to an abutment tooth within the oral cavity and has a socket with an opening attached to the upright wall for removably seating the male member. The appliance is mounted to the male member which includes a laterally extending stop member which positively contacts the upright wall when the male member is seated on the socket of the female member.

More particularly, in the present case, because the dental appliance is often supported on one end thereof or at a single location, when the free or unsupported side is put under pressure, such as during the chewing cycle, undesirable or even destructive force is applied to the abutment tooth via the female member. As has been previously explained in the Sulc '367 patent, the provision of a free gap between the top surface of the socket of the female member and the underside of the base portion of the male member (see FIG. 10), as well as the universal movement capability are needed to accommodate the biting and chewing forces that the appliance experiences, the free gap providing the space for the appliance to move further down. Moreover, the free gap permits the appliance to move downwardly to compress the tissue under the appliance. Because of this downward flexibility, due to the above described free gap, the downward chewing forces are not transmitted directly to the female member and the abutment tooth and thus prevents damage to the abutment tooth.

While the prior art design accommodated the absorption of damaging downwardly directed forces due to chewing, no provision was present for forces and loads applied to the abutment tooth by the uplifting of the free end of the appliance. As can be appreciated, the unsupported end of the appliance is capable of upward, downward, and lateral or "fish-tailing" movement. Such movement is not only undesirable and uncomfortable to the user but can, as a result of these undesirable forces being absorbed by the abutment tooth, damage the same.

The undesirable and damaging forces resulting from the uplifting of the unsupported end of an appliance is overcome by a present male member which includes features that are not shown or suggested by the prior invention. Specifically, the male member is an improvement of the male member of Sulc '367 patent. The male member has a substantially cup-shaped body, including a base, a cylindrical wall extending from the base, a projection extending from the base in the same direction as the cylindrical wall, and a relatively large rectangular stop member that extends laterally from the base and positively contact the upright wall of the female member. This new and improved feature provides an additional stabilizing contact surface and also serves as a stop surface to prevent the male member from undesirably pivoting toward the upright wall of the female member which causes uplifting of the dental appliance.

In addition, the projection is formed in the shape of an hourglass, including a waist section where the two convex curve profiles of the hourglass shape meet to form the narrowest point. The socket of the female member, which is designed to seat the male member with the projection of the male member situated in the opening of the socket, is provided with a contoured constriction in the form of a convex curve profile. The waist section is situated above the narrowest section of the constriction, as shown in FIG. 16, when the male member is fully seated in the socket of the female member to provide a snap fit retention and a mount that will permit a substantial universal movement capability of the male member in relation to the female member, which in turn provides the same movement with the appliance that is attached to the male member. When the male member is fully seated in the socket, the projection is situated so that a gap is formed between the base and the upper entry surface of the socket in a quiescent or non-chewing condition to allow for vertical movements of the male member which supports the appliance to distribute forces generated during the chewing cycle over the entire edentulous ridge area that supports the appliance, which is mounted to the male member.

Accordingly, one object of the invention is to provide a dental structure with a male member having a laterally extending stop member to prevent the movement of the male member toward the female member beyond its neutral position, which in turn prevents uplifting of the free end of the dental structure during the chewing cycle.

Another object of the invention is to provide a male member with a substantial universal movement capability in relation to the female member to distribute forces generated during the chewing cycle over the entire edentulous ridge area that supports the appliance.

Another object of the invention is to provide a male member with a vertical movement capability to distribute forces generated during the chewing cycle over the entire edentulous ridge area that supports the appliance, which is mounted to the male member.

BRIEF DESCRIPTION OF THE INVENTION

DETAILED DESCRIPTION OF THE DRAWINGS

A detailed description of FIGS. 1-12 has been described above in the section entitled Background of the Invention, the description of which has been incorporated herein. The description of the present invention follows below.

Figure 13:
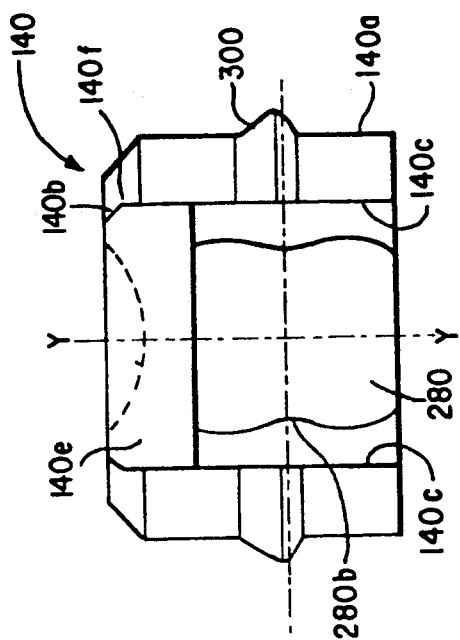
FIG. 13 is a front elevational view of the male member of the present invention.
Figure 15:
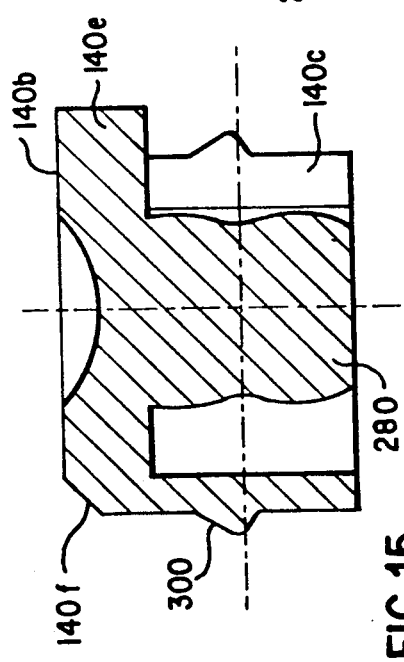
FIG. 15 is a cross-sectional view 15—15 of FIG. 14 of the male member of the present invention.
Figure 14:
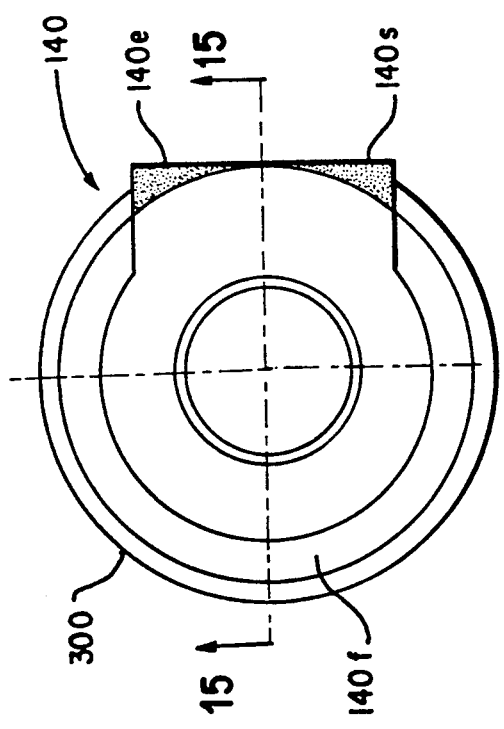
FIG. 14 is a plan view of the male member of the present invention illustrating the rectangular stop member in solid color.
Figure 16:
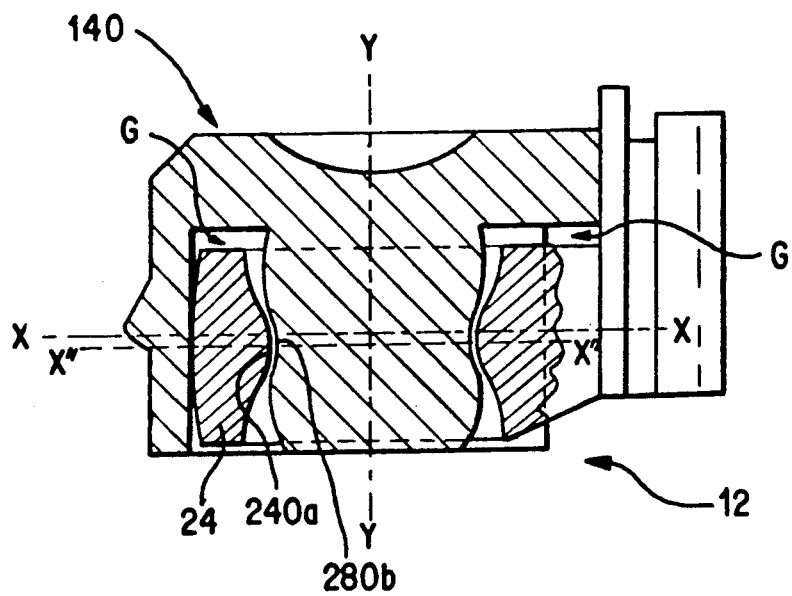
FIG. 16 is a cross-sectional view of the male and female members of the present invention illustrating their relationship.
Figure 17:
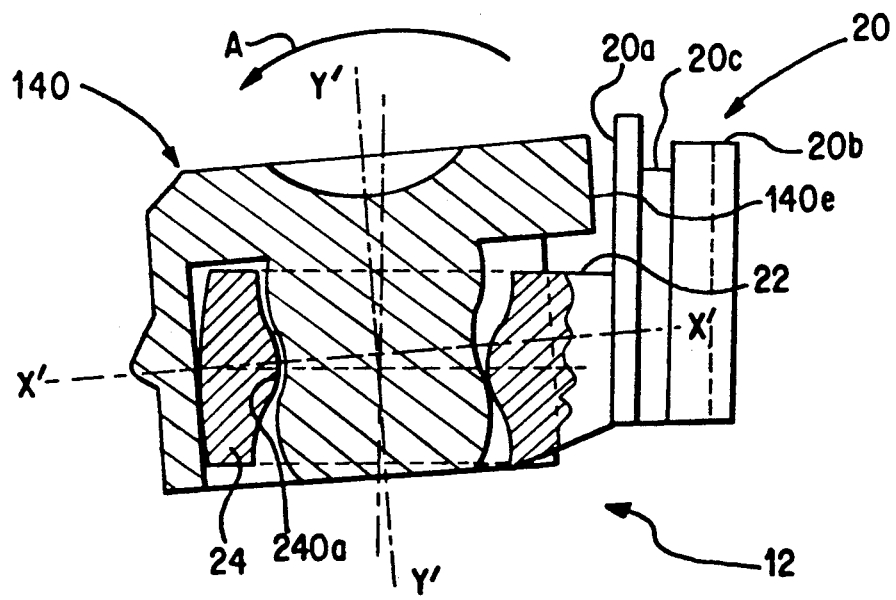
FIG. 17 is a cross-sectional view of the male and female members of the present invention illustrating the rotational capability of the male member with respect to the female member.

FIGS. 13 and 14 show a male member 140 comprising a wall 140*a* which extends from a base 140*b* to form a substantially cup-shaped structure. The wall 140*a* includes a rectangular cut-out 140*c* to accommodate the base 22 which connects the socket 24 to the retention plate 20 of the female member 12. A projection 280 extends from the base 140*b* along the axis Y—Y and has an outer contour substantially shaped in the form of an hourglass, and the hourglass shape is complementary to that of the inner surface of the side wall of the socket 24 of the female member 12 which is shown in FIGS. 16 and 17. The projection has a waist portion 280*b* about the midpoint of its length where two convex curve profiles meet. The waist allows a snap fit retention in the socket 24 and permits a substantial universal movement capability of the appliance which is attached to outer surfaces of the wall 140*a* of the male member as disclosed in the Sulc '367 patent. An arrangement where an appliance is attached to the male member is illustrated in FIGS. 4 and 7.

Figure 1:
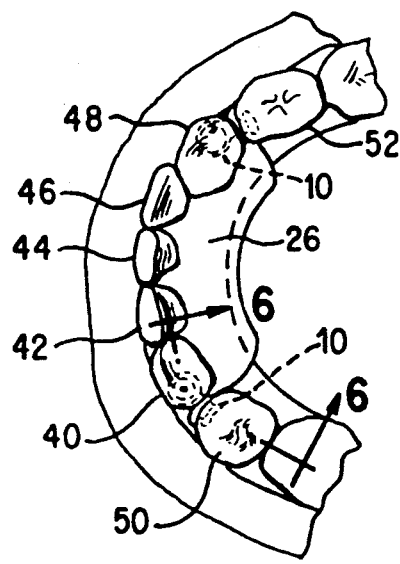
FIG. 1 is a plan view of Prior Art illustrating a portion of the oral cavity and an appliance held in the cavity by a dental attachment structure.
Figure 2:
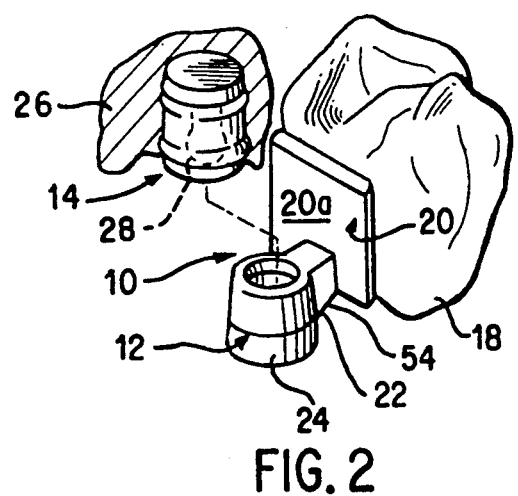
FIG. 2 is a perspective view of Prior Art illustrating the manner of mounting the dental attachment structure.
Figure 3:
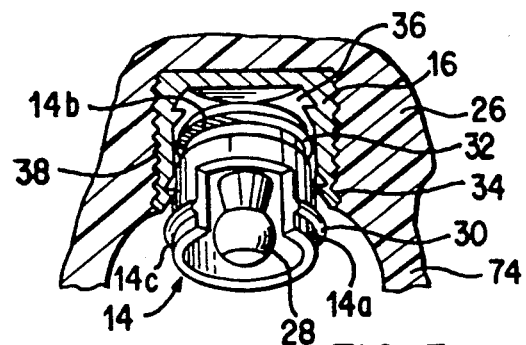
FIG. 3 is a perspective view of the male member of the dental attachment structure of Prior Art.
Figure 6:
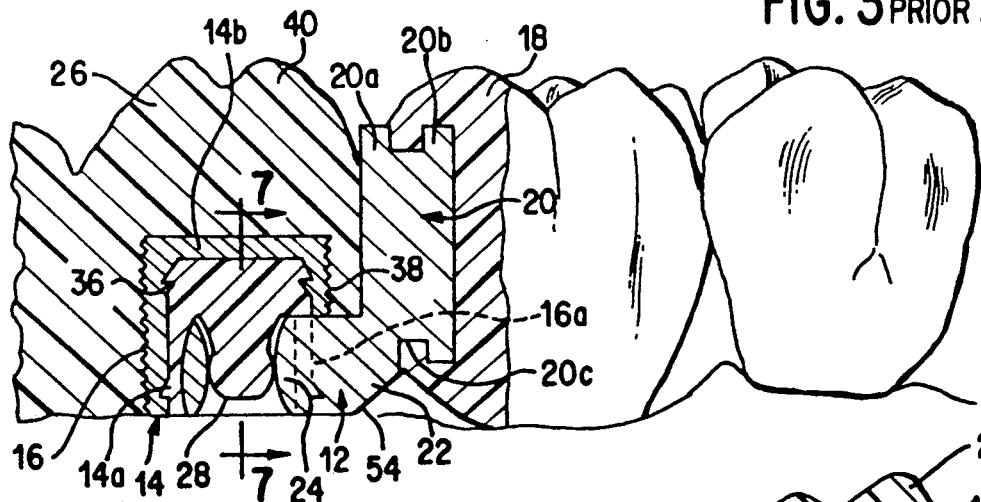
FIG. 6 is a cross-sectional view 6—6 of FIG. 1.
Figure 7:
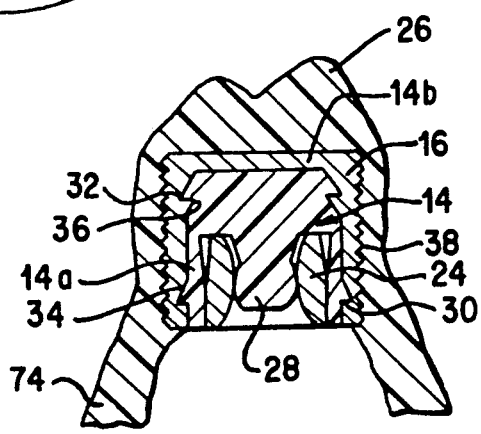
FIG. 7 is a cross-sectional view 7—7 of FIG. 6.
Figure 4:
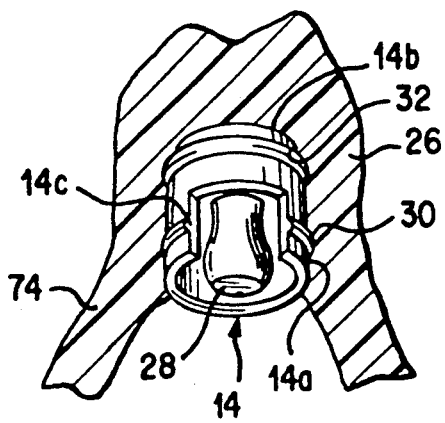
FIG. 4 is a perspective view of the male member of Prior Art illustrating a second manner of mounting the male member to the appliance.
Figure 5:
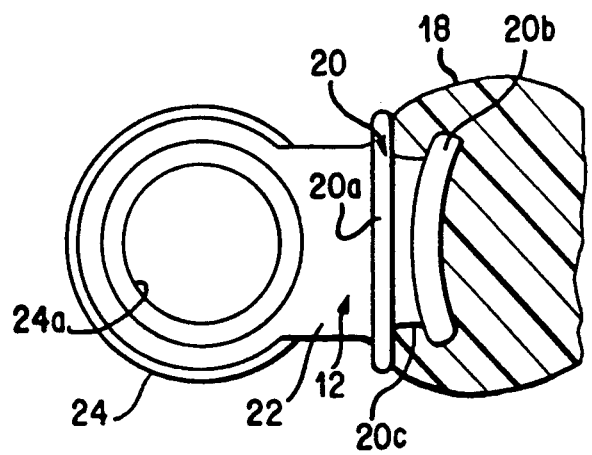
FIG. 5 is a plan view of the female member of the dental structure of Prior Art supported by an abutment tooth.
Figure 8:
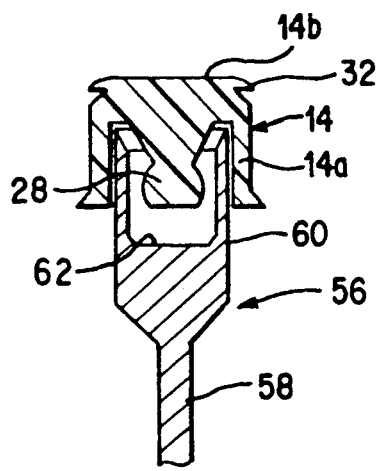
FIG. 8 is a cross-sectional view of the male member of Prior Art and a tool used for removing the male member from the dental appliance.
Figure 9:
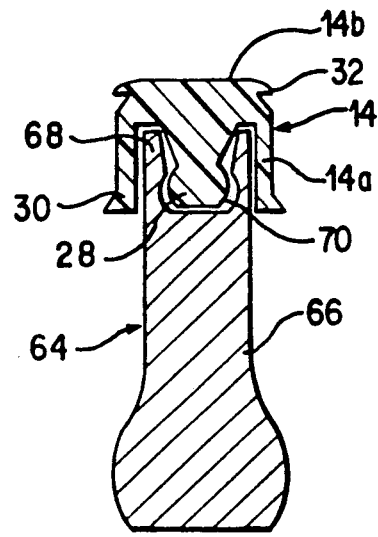
FIG. 9 is a cross-sectional view of the male member of Prior Art and a tool used for seating the male member to the dental appliance.
Figures 10, 11, 12:
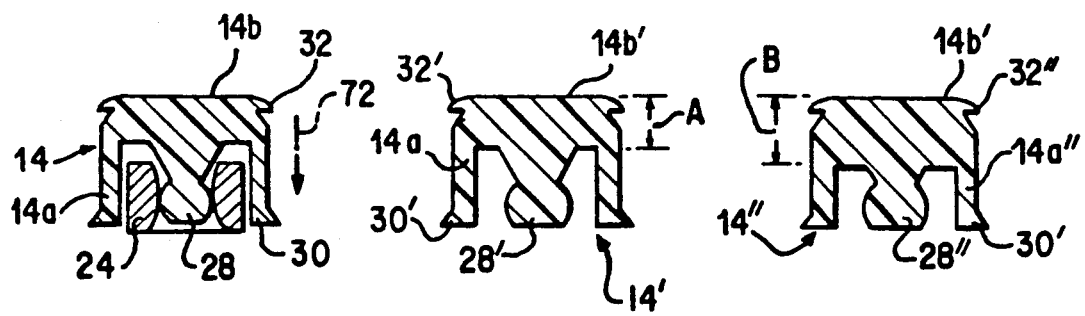
FIG. 10 is a cross-sectional view of the male and female members of Prior Art illustrating their relationship.
FIGS. 11 and 12 are cross-sectional view of the male member of Prior Art illustrating various dimensional variations.

The outer surface of the wall 140*a* of the male member includes an outer ridge ring 300 similar to the outer ring 30 and 32 as shown in FIGS. 4 and 7 to enable the wall to be either embedded directly to the appliance 26 or attached within a support structure 16. The outer surface where the base 140b joins the wall 140a is formed with a bevel 140f, which provides a reduced diameter, for permitting easier entry of the male member in the cavity of the appliance. Furthermore, the base has a relatively large rectangular stop member 140e for abutting an upright sidewall of the female member as more fully described below in reference to FIG. 14.

FIG. 14 is a plan view of the male member showing the stop member 140e more clearly. The shaded solid area 140s is provided for comparison purposes. That is, the male member 14 of the Sulc '367 patent and the APM-Sterngold Catalog is not provided with a stop member, the solid shaded area 140s. It was previously disclosed that the projection 280 is designed to provide a substantial universal movement. However, a pivotal movement of the male member toward the upright wall 20a beyond the neutral 90 degree alignment is not desirable because it results in the lifting of the dental appliance off the edentulous ridge. This lifting causes discomfort to the user and transmits damaging forces by way of the female supporting socket to the abutment tooth. In time, the supporting abutment tooth may be severally weakened and/or extracted.

While the Sulc '367 patent male member leaves an undesirable gap between the upright wall and the outer surface of the male member, the present male member includes a stop member 140e that has been engineered to provide a consistent, built-in positive contact between the stop member of the male member and an adjacent upright wall 20a of the female member at its neutral position when fully seated in the female member as illustrated in FIG. 16.

By providing the stop member disposed against the upright wall 20a, the stop member prevents the male member from pivoting away from the neutral position toward the female member and thus prevents the appliance from pivoting toward the upright wall, which in turn prevents the free end of the appliance from uplifting. The male member, however, is free to pivot away from the upright wall 20a of the female member as illustrated by an arrow A in FIG. 17 so that the free end of the appliance can be supported by the tissue to prevent undue forces from being applied to the abutment tooth and the female member. This pivoting motion is possible because the outer surface of the socket 24 is shaped so that there are sufficient gaps formed between the outer surface of the socket and the inner surface of the cylindrically shaped wall 140a of the male member.

FIGS. 16 and 17 illustrate the relationship between the male and the female members when the male member is fully seated in the socket 24. The axis X—X represents a line drawn through the narrowest section of the waist 280b of the projection 280 and the axis X"—X" represents a line drawn through the convex profiled ridge 240a at which the opening in the side wall socket 24 of the female member 12 is narrowest. The axes Y'—Y' and X'—X' are illustrated to show the relationship between the waist 280b of the projection 280 and the ridge 240a when the male member is rotated away from the neutral position. As clearly shown by axes X—X and X"—X" of FIG. 16, the waist 280b is positioned above the ridge 240a when the male member is fully seated in the socket 24 of the female member to provide a snap fit retention and a mount that will permit a substantial universal movement capability of the male member in relation to the female member, which in turn enables the appliance that is attached to the male member to the same movement. Furthermore, because of the positioning of the waist above the ridge, a tighter interference fit is provided for and the upward movement of the male member in the Y—Y axis direction is restricted since the ridge engages the wider sloped concave portion of the waist area rather than the narrowest point of the waist. At the same time, the specified waist and ridge orientation enables the male member to move toward the socket 24 in the Y—Y direction.

The male member 140 of the present invention functions similarly as the male member as previously disclosed above with respect to the Sulc '367 patent. That is, in a quiescent or non-chewing condition, a gap G is provided between the lower surface of base 14b and the upper surface of the socket. The space allows for movement of the male member which supports the appliance in the Y—Y direction beyond a full snap position of receipt of the male member into the socket. The vertical movement of the appliance is limited by how much the tissue (gums) may compress. When the appliance is seated in the oral cavity, the saddle 74 of the appliance, see FIG. 3, for example, comes into full contact with the gums just as the projection of the male member snaps over the socket of the female member. Then, under additional load on the appliance, during chewing, the appliance can settle and recoil back as the tissue resiliency will allow. In this manner, the forces generated during the chewing cycle are distributed over the entire edentulous ridge area that supports the appliance. If the fit between the male and female members of the connector 10 was a totally rigid snap fit, the appliance would not be able to move down and be supported by the tissue. Consequently, all the extra force would have to be absorbed by the abutment tooth, thereby causing excessive stress on the abutment tooth and the female member that supports the appliance, which can also cause excessive wear to the female member. The dimension of the gap G will equal the maximum possible additional downward movement that the appliance may undergo during the chewing cycle.

The foregoing description is only illustrative of the principle of the present invention. It is to be understood that the present invention is not to be limited to the exact construction as illustrated and described herein. Accordingly, all expedient modifications which may be made within the scope and the spirit of the present invention are encompassed herein.

I claim:

1. In a dental structure for removably mounting a dental appliance, which includes a partial denture, a bridge, or a similar dental appliance, in an oral cavity, comprising a female member having an upright wall attached to an abutment tooth within said oral cavity and having a socket attached to said upright wall for removably seating a male member, and said dental appliance having a cavity for accommodating said male member therein, the improvement wherein said male member comprises:

a substantially cup-shaped body having a base, a cylindrical wall extending from said base, and a projection extending from the base in the same general direction as said wall; and a stop member having an end surface projecting laterally from said base, whereby said end surface positively contacts said upright wall of said female member for providing an additional stabilizing contact surface and serving as a stop surface to prevent said male member from pivoting toward said upright wall of said female member.

2. A dental structure according to claim 1, wherein said female member further comprises a base extension having a free end extending from a lower portion of said upright wall, said socket being attached to said free end of said base portion.

3. A dental structure according to claim 2, wherein said male member further comprises a cut-out section in said cylindrical wall for accommodating said base extension within the region of said socket.

4. A dental structure according to claim 3, wherein said male member further comprises a bevel at said base to permit an easier entry of said male member within said cavity of said dental appliance.

5. A dental structure according to claim 4, wherein said projection is shaped substantially in the form of an hourglass, including a waist at the midpoint of the projection where two convex curve profiles of said hourglass shape meet.

6. A dental structure according to claim 1, wherein said end surface is a flat planar surface which is substantially parallel and contacting with the surface of the upright wall when said male member is seated in said female member.

7. In a dental structure of removably mounting a dental appliance, which includes a partial denture, a bridge, or a similar dental appliance, in an oral cavity, comprising a female member having an upright wall attached to an abutment tooth within said oral cavity and having a socket attached to said upright wall for removable seating a male member, and said dental appliance having a cavity for seating said male member, the improvement wherein,
said male member comprises:
a substantially cup-shaped body having a base, a cylindrical wall extending from said base, and a projection extending from the base is the same general direction as said wall;
a stop member having an end surface projecting laterally from said base,
whereby said said end surface positively contacts said upright wall of said female member for providing an additional stabilizing contact surface and serving as a stop surface to prevent said male member from pivoting toward said upright wall of said female member;
said projection being shaped substantially in the form of an hourglass, including a groove at the midpoint of the projection where two convex curve profiles of said hourglass shape meet; and
said female member comprises:
a convex profiled ridge formed inside said socket for providing a complementary snap retention fit with said substantially hour-glass shape projection.

8. A dental structure according to claim 7, wherein said female member further comprises a base extension having a free end extending from a lower portion of said upright wall, said socket being attached to said free end of said base portion.

9. A dental structure according to claim 8, wherein said male member further comprises a cut-out section in said cylindrical wall for accommodating said base extension within the region of said socket.

10. A dental structure according to claim 9, wherein said male member further comprises a bevel at said base to permit an easier entry of said male member within said cavity of said dental appliance.

11. A dental structure according to claim 7, wherein said groove is situated above said ridge when said male member is fully seated in said socket of said female member.

12. A dental structure according to claim 7, wherein said end surface is a flat planar surface which is substantially parallel and contacting with the surface of the upright wall when said male member is seated in said female member.

13. A male member which is seated within a cavity, a dental appliance, which includes a partial denture, a bridge, or a similar dental appliance, in an oral cavity, and for mounting to a socket of a female member having an upright wall, comprising:
a substantially cup-shaped body having a base, a cylindrical wall extending from said base, and a projection extending from the base in the same general direction as said wall; and
a stop member having an end surface projecting laterally from said base,
whereby said end surface positively contacts said upright wall of said female member for providing an additional stabilizing contact surface and serving as a stop surface to prevent said male member from pivoting toward said upright wall of said female member.

14. A dental structure according to claim 13, wherein said male member further comprises a cut-out section in said cylindrical wall.

15. A dental structure according to claim 14, wherein said male member further comprises a bevel at said base to permit an easier entry of said male member within said cavity of said dental appliance.

16. A dental structure according to claim 15, wherein said projection is shaped substantially in the form of an hourglass, including a groove at the midpoint of the projection where two convex curve profiles of said hourglass shape meet.

17. A dental structure according to claim 13, wherein said end surface is a flat planar surface which is substantially parallel and contacting with the surface of the upright wall when said male member is seated in said female member.

* * * * *

UNITED STATES PATENT AND TRADEMARK OFFICE
CERTIFICATE OF CORRECTION

PATENT NO. :   5,120,222

DATED      :   June 9, 1992

INVENTOR(S) :   Josef M. Sulc

It is certified that errors appear in the above-identified patent and that said Letters Patent is hereby corrected as shown below:

Column 11,
        Claim 7, line 27, replace "of" with --for--;
        Claim 7, line 39, replace "is" with --in--;
Col. 12, claim 13, line 23, replace "which is seated" with --for seating--
Col. 12, claim 13, line 23, replace "," with --of--

Signed and Sealed this

Fourteenth Day of September, 1993

Attest:

BRUCE LEHMAN

*Attesting Officer*       *Commissioner of Patents and Trademarks*